July 22, 1969 R. S. MOORE Plant Pat. 2,911
MINIATURE ROSE PLANT
Filed Sept. 22, 1967
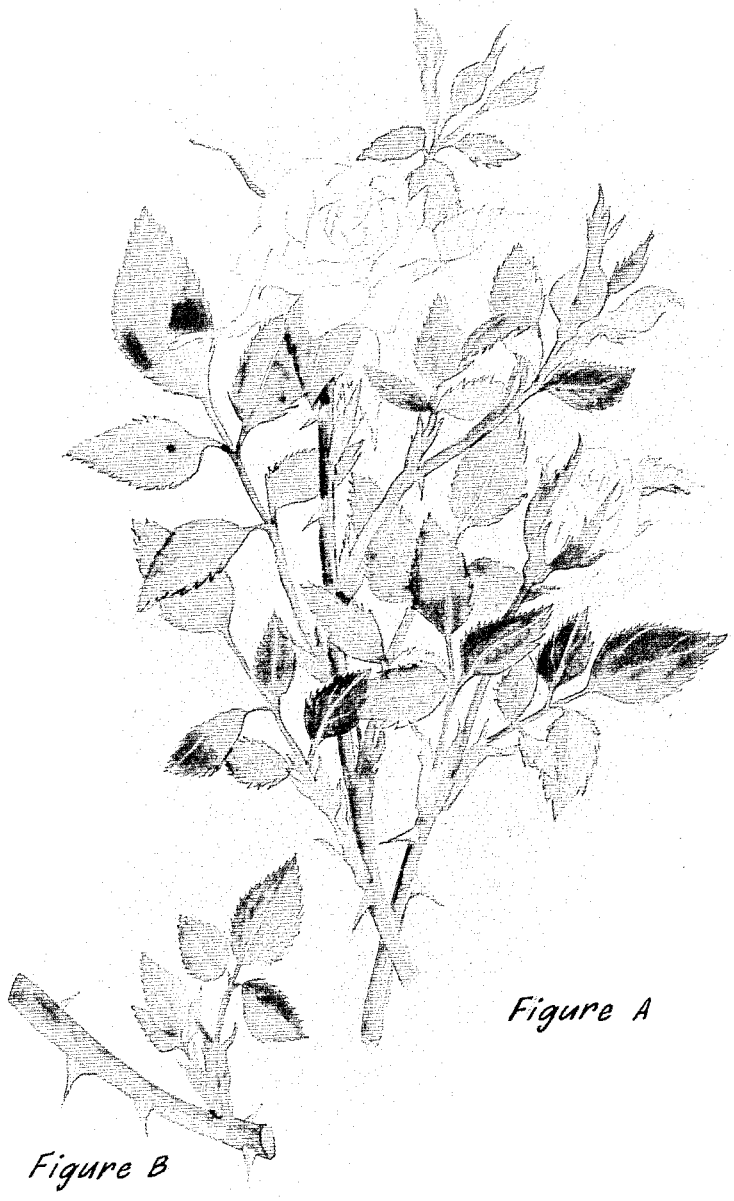
Figure A
Figure B
WITNESS
Jeanette Nunn Copley
INVENTOR
Ralph S. Moore

United States Patent Office

Plant Pat. 2,911
Patented July 22, 1969

2,911

MINIATURE ROSE PLANT

Ralph S. Moore, 2519 E. Noble Ave.,
Visalia, Calif. 93277

Filed Sept. 22, 1967, Ser. No. 669,982
Int. Cl. A01h *5/00*
U.S. Cl. Plt.—8 1 Claim The present invention relates to a new and distinct variety of hardy, dwarf, bush type rose plant of the miniature class; the variety being primarily characterized, as to novelty, by buds and flowers in an unusual and heretofore unknown, for miniatures, shade of soft apricot coloring.

The variety is further characterized by:

An abundance of bloom, with flowers usually borne singly but sometimes in loose clusters of 3 or more to the stem. A plant which is vigorous, of low rounded habit, with dull medium green leaves; a plant which has a normal average height of 10″ to 12″ at maturity, resembles the general plant habit of Easter Morning (Pl. Patent 2,177), the bud and flower being similar to Easter Morning but smaller in size and the color of the present variety being soft apricot rather than white or near white.

A plant which grows and blooms satisfactorily both in the greenhouse and outdoors; is a good plant for growing in pots; and provides excellent garden decoration as well as cut flowers.

The present variety of miniature rose was originated by me in my nursery, located at Visalia, Calif., under conditions of careful control and observation, as a cross between Golden Glow, a large flowered climbing rose (Plant Patent 236—expired), as the seed parent and Zee, a miniature rose (not patented), as the pollen parent.

Subsequent to origination of the variety I successfully asexually reproduced it, in my nursery located as aforesaid, by budding as well as by cuttings; the reproductions having run true in all respects.

The figure of the drawing illustrates a spray, including foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bush; seedling; greenhouse; outdoors; cut flowers; garden decoration; potted plant.

Class: Miniature.

Flower:

*Continuity.*—Continuous.

*Fragrance.*—Sweet, tea rose.

Flowers borne: Singly and several together on slender, wiry stems.

Quantity of bloom: Abundant bloom both outside and in greenhouse.

Bud: Peduncle—medium length; slender; erect; light to medium green; few very short prickles (or hairs). Before calyx breaks: size—small. Form—pointed; with few and very insignificant foliaceous appendages on surface of bud and foliaceous parts extending beyond the tip of the bud equal to one half or more of its length. Color—medium green. As calyx breaks—color orange (or orange-red) shading to yellow or greenish yellow at base; size—small. Form—medium long, sometimes ovoid; becoming somewhat urn shaped as bud expands. Opening—opens well in all weather.

Bloom:

*Size when fully open.*—Small, 1⅛″ to 1⅜″.

*Petalage.*—Very double—usually with about 20 larger petals and 20 to 25 smaller petals.

*Form.*—Center rounded, moderately high.

Petals: Moderately thick; satiny both inside and outside; outer petals tend to roll outward thus becoming pointed. Shape: outside petals broad lanceolate with rounded tip; intermediate petals broad lanceolate with acute tip; inside petals lanceolate with acute tip.

Color: Newly opened flower from plant grown outdoors (September, 1967), Visalia, Calif.

*Outside petal.*—Outside surface—Apricot 609/2 shading into greenish yellow at base; inside surface, Apricot 609/2 shading into Maize Yellow 607/2 thence into Maize Yellow 607/1 at base.

*Intermediate petal.*—Outside surface—same as above; inside surface—same as above.

*Inside petal.*—Outside surface—same as above; inside surface—same as above.

*General color effect newly opened flower.*—Soft apricot, sometimes with just a hint of grey. Three days open—lighter color, usually with soft pink.

*Behaviour.*—Spent blooms persist for a time before petals fall.

*Flower longevity* (September 1967—outdoors). Bush in garden or in pot—3 to 5 days. In cooler weather of fall flowers may last 5 to 7 days with color aging darker pink. Cut flowers at living room temperatures—3 days.

Reproductive organs:

*Stamens.*—Few, mixed with petaloids.

*Filaments.*—Yellow.

*Pollen.*—None.

*Pistils.*—Average length and number.

*Styles.*—Medium length, uneven, bunched, pale green.

*Stigma.*—Usually deformed or missing.

*Ovaries.*—All enclosed in calyx.

*Hips.*—None.

*Sepals.*—Permanent; spear shaped.

*Seeds.*—None.

Foliage:

*Leaves.*—Compound of five leaflets (occasionally 3); abundant; small, medium thickness, dull green.

*Leaflets.*—Shape—broad lanceolate; apex acute; base rounded; margin serrate. Color—medium green; new growth green or lightly tinted reddish. Rachis—medium strength; upper side grooved; under side sparsely horny. Stipules—relatively short; short points turning out at angle of about 45 degrees.

Growth:

*Habit.*—Dwarf; bushy; rounded: much branched.

*Growth.*—Vigorous.

*Canes.*—Medium; slender.

*Main stems.*—Color—medium green. Thorns—moderately thorny; slender; medium length; almost straight; color—medium-brown or grey-brown; medium length oval base. Prickles—none. Hairs—none.

*Branches.*—Color—medium green. Thorns—moderately thorny; medium length; straight; medium length oval base. Prickles—none. Hairs—none.

*New shoots.*—Color—medium green. Thorns—moderately thorny; straight; short oval base; color—pale pink or pinkish green. Prickles—none. Hairs—none.

The miniature rose plant and its flowers as herein described may vary in slgiht detail due to climatic, soil and cultural conditions under which the variety may be grown; the present description being of the variety as grown at Visalia, Calif.

The following is claimed:

1. A new and distinct variety of miniature rose plant of hardy, dwarf, rounded, much branched, bush type, as illustrated and described, characterized by buds and flowers resembling the Easter Morning miniature rose (Pl. Patent 2,177) in general form, but of an unique shade of soft apricot coloring, the general color effect of the freshly opened flower being soft apricot; and further characterized by a plant of vigorous and compact growth, easy to propagate from both soft and hard wood cuttings; abundant pliable roots which facilitate potting and transplanting; small medium green foliage, an abundance of bloom borne almost continuously throughout the growing season with flowers borne singly and in loose small clusters.

No references cited.

ROBERT E. BAGWILL, Primary Examiner